(12) United States Patent
De Wilde et al.

(10) Patent No.: US 10,071,072 B2
(45) Date of Patent: Sep. 11, 2018

(54) METHOD FOR TREATING NEUROTRAUMA

(71) Applicant: N.V. Nutricia, Zoetermeer (NL)

(72) Inventors: Mattheus Cornelis De Wilde, Utrecht (NL); Johannes Wilhelmus Christina Sijben, Utrecht (NL); Patrick Joseph Gerardus Hendrikus Kamphuis, Utrecht (NL); Robert Johan Joseph Hageman, Utrecht (NL)

(73) Assignee: N.V. NUTRICIA, Zoetermeer (NL)

( * ) Notice: Subject to any disclaimer, the term of this patent is extended or adjusted under 35 U.S.C. 154(b) by 60 days.

(21) Appl. No.: 15/417,943

(22) Filed: Jan. 27, 2017

(65) Prior Publication Data

US 2017/0135975 A1 May 18, 2017

Related U.S. Application Data

(63) Continuation of application No. 14/005,098, filed as application No. PCT/NL2012/050158 on Mar. 14, 2012, now Pat. No. 9,579,336.

(30) Foreign Application Priority Data

Mar. 14, 2011 (NL) ................. PCT/NL2011/050176

(51) Int. Cl.
| | | |
|---|---|---|
| *A61K 31/00* | (2006.01) |
| *A61K 9/00* | (2006.01) |
| *A61K 31/202* | (2006.01) |
| *A61K 31/7072* | (2006.01) |
| *A61K 31/7068* | (2006.01) |
| *A61K 31/14* | (2006.01) |
| *A61K 31/714* | (2006.01) |
| *A61K 31/675* | (2006.01) |
| *A61K 31/519* | (2006.01) |
| *A61K 31/375* | (2006.01) |
| *A61K 31/355* | (2006.01) |
| *A61K 31/661* | (2006.01) |
| *A61K 33/04* | (2006.01) |

(52) U.S. Cl.
CPC ............ *A61K 31/202* (2013.01); *A61K 31/14* (2013.01); *A61K 31/355* (2013.01); *A61K 31/375* (2013.01); *A61K 31/519* (2013.01); *A61K 31/661* (2013.01); *A61K 31/675* (2013.01); *A61K 31/7068* (2013.01); *A61K 31/7072* (2013.01); *A61K 31/714* (2013.01); *A61K 33/04* (2013.01)

(58) Field of Classification Search
CPC .............. A61K 9/0095; A61K 2300/00; A61K 31/202; A61K 31/205; A61K 31/355; A61K 31/375; A61K 31/519; A61K 31/685; A61K 31/714; A61K 31/4415; A61K 31/7068; A61K 31/7072; A23V 2002/00; A23D 7/003

USPC .......................................................... 514/51
See application file for complete search history.

(56) References Cited

U.S. PATENT DOCUMENTS

| | | | | |
|---|---|---|---|---|
| 5,308,832 A | * | 5/1994 | Garleb ................. | A61K 36/02 426/656 |
| 5,874,470 A | * | 2/1999 | Nehne ................. | A61K 31/20 514/458 |
| 8,361,989 B2 | | 1/2013 | Groenendijk et al. | |
| 8,497,238 B2 | | 7/2013 | Hageman et al. | |
| 8,791,089 B2 | | 7/2014 | Groenendijk et al. | |
| 2004/0014721 A1 | | 1/2004 | Hensley et al. | |
| 2005/0203053 A1 | | 9/2005 | Wurtman et al. | |
| 2010/0292330 A1 | | 11/2010 | Pan et al. | |
| 2011/0257267 A1 | * | 10/2011 | Hadley ................. | A61K 31/232 514/547 |

FOREIGN PATENT DOCUMENTS

| | | | |
|---|---|---|---|
| EP | 2 145 637 A1 | 1/2010 | |
| JP | 2005-533042 A | 11/2005 | |
| JP | 2010-540636 A | 12/2010 | |
| WO | WO-2006/031683 A2 | 3/2006 | |
| WO | WO-2006/127620 A2 | 11/2006 | |
| WO | WO-2007/073178 A2 | 6/2007 | |
| WO | WO-2007/089703 A2 | 8/2007 | |
| WO | WO-2009/002165 A1 | 12/2008 | |
| WO | WO 2009/059306 A1 * | 5/2009 | ............ A01N 65/00 |
| WO | WO-2009/059306 A1 | 5/2009 | |

OTHER PUBLICATIONS

The Merck Manual, 1992, 16th Ed., pp. 2263-2264.*
O'Shea, Clin. Obstet. Gynecol. 2008, 51(4), 816-828.*
Michael-Titus, Clin. Lipidology, 2009, 4(3), 343-353.*
Singh, Indian Pediatrics, 2003, 40, 213-220.*
International Preliminary Examination Report dated Jun. 6, 2013 in International Application No. PCT/NL2012/050158.
International Search Report dated Apr. 27, 2012 in International Application No. PCT/NL2012/050158.
Lim et al., "The acute administration of eicosapentaenoic acid is neuroprotective after spinal cord compression injury in rats", Prostaglandins, Leukotrienes and Essential Fatty Acids, 2010, vol. 83, pp. 193-201.

(Continued)

*Primary Examiner* — Ganapathy Krishnan
(74) *Attorney, Agent, or Firm* — Gilberto M. Villacorta; Sunit Talapatra; Foley & Lardner LLP

(57) ABSTRACT

The invention relates to a composition comprising:
i) one or more of uridine and cytidine, or salts, phosphates, acyl derivatives or esters thereof;
ii) a lipid fraction comprising at least one of docosahexaenoic acid (22:6; DHA), eicosapentaenoic acid (20:5; EPA) and docosapentaenoic acid (22:5; DPA), or esters thereof, in which the lipid fraction comprises less than 2 weight % of α-linolenic acid (ALA), calculated on the weight of all fatty acids;
iii) choline, or salts or esters thereof;
for use in the prevention or treatment of neurotrauma, traumatic brain injury, cerebral palsy and spinal cord injury.

23 Claims, 3 Drawing Sheets

(56) References Cited

OTHER PUBLICATIONS

Michael-Titus "Omega-3 Fatty Acids: Their Neuroprotective and Regenerative Potential in Traumatic Neurological Injury", Clin. Lipidology (2009) vol. 4, No. 3, pp. 343-353.
O'Shea "Diagnosis, Treatment, and Prevention of Cerebral Palsy in Near-Term/Term Infants", Clin Obstet. Gynecol. (Dec. 2008) vol. 51, No. 4, pp. 816-828.
Petchkrua et al., "Prevalence of vitamin B12 deficiency in spinal cord injury", Arch Phys Med Rehabil, Nov. 2003, vol. 84, pp. 1675-1679.
Singh "Nutrition, Brain and Environment: How to Have Smarter Babies?" Indian Pediatrics (2003) vol. 40, pp. 213-220.
The Merck Manual of Diagnosis and Therapy (1992), published by Merck Research Laboratories, 16th Ed., pp. 2263-2264.
Titus, "Omega-3 fatty acids and neurological injury", Protaglandins Leukotrienes & Essential Fatty Acids, 2007, vol. 77, pp. 295-300.

\* cited by examiner

METHOD FOR TREATING NEUROTRAUMA

CROSS-REFERENCE TO RELATED APPLICATIONS

This application is a Continuation application of U.S. patent application Ser. No. 14/005,098, filed Nov. 19, 2013, which is the National Phase of International Patent Application No. PCT/NL2012/050158, filed Mar. 14, 2012, published on Nov. 13, 2014 as WO 2012/125034 A1, which claims priority to International Patent Application No. PCT/NL2011/050176, filed Mar. 14, 2011. The contents of these applications are herein incorporated by reference in their entirety.

The invention is in the field of medical nutrition and more particularly relates to a composition for use in the treatment of neurotraumas such as spinal cord injury (SCI) and cerebral palsy (CP).

BACKGROUND DESCRIPTION

During the last decennium, uridine, choline and omega-3 fatty acids such as DHA have attracted attention as active components in treating cognitive dysfunction and age-associated memory impairment (AAMI). These compounds are rate-limiting precursors for membrane phosphatide synthesis.

WO2007/089703 (Massachusetts Institute of Technology) discloses uridine for treating AAMI, hippocampal dysfunction, memory disorders and brain damage, comprising a composition comprising uridine. In one embodiment, the composition comprising the uridine has a lipid fraction comprising docosahexaenoic acid, eicosapentaenoic acid, docosapentaenoic acid, or a combination thereof. Other than fish oil, the fat fraction is left unspecified. In one embodiment, this publication discloses a composition comprising UMP, choline, fish oil, carbohydrate and milk protein, without linking it to a particular neurological disorder.

WO 2009/059306 (Massachusetts Institute of Technology) provides a method of evaluating a subject's compliance with a uridine dietary supplementation regimen, using magnetic resonance imaging (MRI). Dietary supplementation may further include choline and omega-3 fatty acids such as DHA. This publication is concerned with measuring brain cytidine levels, but does not provide any treatment in itself.

WO 2009/002165 (N.V. Nutricia) discloses a lipid fraction for improving brain function. The focus is on neurological disorders such as Alzheimer's disease and decrease in cognitive function, in which case the composition may further comprise UMP. The lipid composition involves a specific ratio of medium-chain fatty acids hexanoic acid and octanoic acid, and furthermore comprises DHA and EPA. There should be more than 0.4 g alpha-linolenic acid per 100 g fatty acids present. Additionally, this publication teaches that the amount of the sum of C6:0+C7:0+C8:0 fatty acids to the sum of C9:0+C10:0 is at least 2.5:1.

WO 2007/073178 (N.V. Nutricia) discloses a composition comprising a) DHA, DPA and/or EPA in combination with b) a protein fraction providing cysteine and/or taurine, and c) a mineral fraction comprising at least one of manganese and molybdenum, for use in the treatment of neurological disorders, improvement of function of nerve cells, decrease in the formation of plaques, neuropathies, and the improvement of function of the nerve system. Uridine and choline are listed as further components.

The effect of a medical food containing a cocktail of DHA/EPA, uridine, choline, phospholipids and vitamins B, C and E such as disclosed in WO 2007/073178 as mentioned above on cognitive function was investigated in a clinical trial with people with mild Alzheimer's disease. The results are reported in Scheltens et al., *Alzheimer's & Dementia* 6 (2010), 1-10. Significant improvement in the delayed verbal recall task was noted.

Where a medical nutrition is developed in the prior art to prevent and treat dementia syndromes and cognitive dysfunction associated therewith, less attention has been drawn to another class of neurological disorders, i.e. those caused by neurotrauma. Neurotrauma involves traumatic injury to either the brain or spinal cord. Neurological trauma causes thousands of deaths and devastating irreversible tragedies annually. Because it afflicts many otherwise perfectly healthy young people, the productive years lost as a result of its ravages are particularly high. Although these neurological disorders share many of the concepts underlying neurodegenerative mechanism also observed for dementia syndromes, there are specific problems associated with the target group of patients.

The problem to be solved is related to the abilities of a patient which suffers from SCI, CP or neurotrauma and the clinical need to improve the recovery of function of the injured nervous tissue after the damage was done. The patient may have difficulties consuming a nutritional product properly (due to partial paralysis of muscles needed for consumption) and many patients suffering from the symptoms from SCI or neurotrauma will experience volume restrictions, loss of appetite and a disturbed taste sensation. It is also a problem to such patient that their activities of daily living, for example their capabilities to use the bathroom are limited. It is therefore a purpose of the invention to solve at least one of these problems and preferably at least 2 or even 3 of these problems simultaneously.

It is noted that merely eliminating (nutritional) ingredients from the nutritional composition taught in the art for treating AD patients may result in a low-volume dosage form, but unfortunately at the cost of the neurodegenerative effect. It is suboptimal to lower the amounts of the active ingredients to meet volume criterions. The art thus searches for other solutions.

SUMMARY OF THE INVENTION

The inventors have observed that after administration of a product comprising (i) one or more of uridine and cytidine, or salts, phosphates, acyl derivatives or esters thereof, (ii) a lipid fraction comprising at least one of docosahexaenoic acid (22:6; DHA), eicosapentaenoic acid (20:5; EPA) and docosapentaenoic acid (22:5; DPA), or esters thereof, in which the lipid fraction comprises less than 2 weight % of α-linolenic acid (ALA), calculated on the weight of all fatty acids, (iii) choline, or salts or esters thereof, neural survival following neurological injury induced by an external force is increased (FIG. 2). This is particularly relevant to conditions characterized by neuronal death and suboptimal neuronal survival. Such conditions include neurotrauma, traumatic brain injury, spinal cord injury, cerebral palsy or other mechanistic events causing injury to the brain, like surgical measures, e.g. those occurring after brain tumor surgery. The Basso, Beattie and Bresnahan (BBB) open-field locomotor test is a respected model in the art advocated as a tool for studying the outcome of spinal cord injury and was used to demonstrate the findings.

Also, it was observed that with the composition according to the invention macrophage recruitment at the site of the injury is significantly decreased following neurological injury induced by an external force. It is well known that macrophages are recruited as a result of tissue damage and are involved in the inflammatory response and immune response. A lower rate of recruitment therefore is related to the presence of a lower rate of tissue damage and inflammation. Attention is drawn to FIG. 4 attached. The lower degree of inflammation after administration of the composition of the invention to a mammal which experienced damage to its nervous tissue can also be demonstrated by considering the amount of oligodendrocytes in the affected area of the nervous tissue. As shown in FIG. 6 enclosed, this appeared to be significantly increased using the composition of the invention. The composition according the invention can therefore be used in the treatment of an inflammatory condition of an injured or damaged nervous tissue, preferably a brain tissue or a part of the spinal cord. The damage to the nervous tissue can be the result of a mechanical force applied to the tissue, like during combating, during child birth, or due to an accident.

The results are surprising, particularly if noticed that the effects of the combination of uridine, DHA and choline as taught in the art for treatment of dementia were limited. This conclusion can be drawn from FIG. 1. A comparison of the results in FIGS. 1 and 2 is possible after correcting for the Control 'BBB score' in each case. From the results attached, it was also concluded that fortification with cysteine-taurine sources and additional mineral fractions with Mn or Mo as taught in the art were not mandatory for use in the treatment of neurotrauma/SCI/CP.

LIST OF PREFERRED EMBODIMENTS

Figure 1:
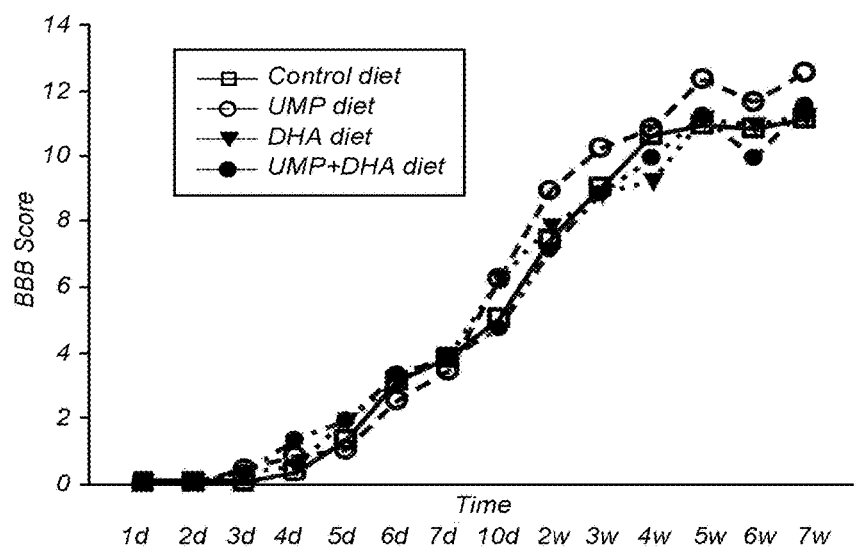
FIG. 1 shows the BBB score (locomotor recovery after SCI) over a period of 7 weeks for control (squares), UMP diet (hollow circles), DHA diet (triangles) and UMP+DHA diet (solid circles). No significant difference can be observed.

According to one embodiment, the composition comprises:
i) one or more of uridine and cytidine, or salts, phosphates, acyl derivatives or esters thereof;
ii) a lipid fraction comprising at least one of docosahexaenoic acid (22:6; DHA), eicosapentaenoic acid (20:5; EPA) and docosapentaenoic acid (22:5; DPA), or esters thereof, in which the lipid fraction comprises less than 2 weight % of α-linolenic acid (ALA), calculated on the weight of all fatty acids;
iii) choline, or salts or esters thereof;
for use in the prevention or treatment of neurotrauma, traumatic brain injury, cerebral palsy and spinal cord injury.

According to another embodiment, the composition according to the invention comprises a lipid fraction comprising medium chain fatty acids (MCT), wherein the sum of MCT C6:0+C7:0+C8:0 over the sum of C9:0 and C10:0 is less than 2:1.

According to another embodiment, said lipid fraction comprises less than 2 weight % fatty acids of less than 14 carbon atoms, based on total fatty acids.

According to another embodiment, the composition according to the invention further comprises less than 25 mg of the sum of cysteine and taurine per 100 ml of the composition.

According to another embodiment, the composition according to the invention comprises linoleic acid (LA) which is present in an amount of less than 15 g/100 g fatty acids.

According to another embodiment, the composition according to the invention further comprises at least one vitamin B selected from the group of vitamin B6, vitamin B12 and vitamin B9, or equivalents thereof, preferably comprising vitamin B6, B9 and B12.

According to another embodiment, the composition according to the invention comprises a lipid fraction comprising 9 to 300 mg/100 kJ DHA+EPA+DPA, preferably DHA+EPA per day.

According to another embodiment, the composition according to the invention comprises 1.5 to 130 mg/100 kJ of one or more of uridine, cytidine, or salts, phosphates or esters thereof, calculated as uridine and cytidine.

According to another embodiment, the composition according to the invention comprises 1 to 300 mg/100 kJ of choline, or salts or esters thereof, calculated as choline.

According to another embodiment, the composition according to the invention further comprises one or more selected from the group consisting of vitamin C or its equivalents, vitamin E or its equivalents, and selenium.

According to another embodiment, the composition according to the invention further comprises at least one phospholipid.

According to another embodiment, the composition according to the invention is provided as a nutritional product.

According to another embodiment, the composition according to the invention is provided as a pharmaceutical product.

According to another embodiment, an aqueous liquid composition according to the invention is provided, said composition comprising, per 100 ml of liquid:
100-500 mg EPA,
1000-1500 mg DHA,
80-600 mg phospholipids,
200-600 mg choline,
400-800 mg UMP (uridine monophosphate),
20-60 mg vitamin E (alpha-TE),
60-100 mg vitamin C,
40-80 μg selenium,
1-5 μg vitamin B12,
0.5-2 mg vitamin B6, and
200-600 μg folic acid.

According to another embodiment, a kit of parts is provided, comprising i) one or more of uridine and cytidine, or salts, phosphates or esters thereof;

ii) a lipid fraction comprising at least one of docosahexaenoic acid (22:6; DHA), eicosapentaenoic acid (20:5; EPA) and docosapentaenoic acid (22:5; DPA), in which the lipid fraction comprises less than 2 weight % of α-linolenic acid (ALA), calculated on the weight of all fatty acids;

iii) choline, or salts or esters thereof;

for use in the prevention or treatment of neurotrauma, traumatic brain injury, cerebral palsy and spinal cord injury.

DETAILED DESCRIPTION OF THE INVENTION

In one aspect of the present invention, the composition according to the invention may be used as a pharmaceutical product comprising one or more pharmaceutically acceptable carrier materials.

In another aspect of the present invention, the composition according to the invention may be used as a nutritional product, for example as a nutritional supplement, e.g., as an additive to a normal diet, as a fortifier, to add to a normal diet, or as a complete nutrition.

The pharmaceutical product, preferably for enteral application, may be a solid or liquid galenical formulation. Examples of solid galenical formulations are tablets, capsules (e.g. hard or soft shell gelatine capsules), pills, sachets, powders, granules and the like which contain the active ingredient together with conventional galenical carriers. Any conventional carrier material can be utilized. The carrier material can be organic or inorganic inert carrier material suitable for oral administration. Suitable carriers include water, gelatine, gum Arabic, lactose, starch, magnesium stearate, talc, vegetable oils, and the like. Additionally, additives such as flavouring agents, preservatives, stabilizers, emulsifying agents, buffers and the like may be added in accordance with accepted practices of pharmaceutical compounding. While the individual active ingredients are suitably administered in a single composition, they may also be administered in individual dosage units. Hence, the invention further relates to a kit of parts comprising i) one or more of uridine and cytidine, or salts, phosphates, acyl derivatives or esters thereof; ii) a lipid fraction comprising at least one of docosahexaenoic acid (22:6; DHA), eicosapentaenoic acid (20:5; EPA) and docosapentaenoic acid (22:5; DPA), or esters thereof, in which the lipid fraction comprises less than 2 weight % of α-linolenic acid (ALA), calculated on the weight of all fatty acids; and iii) choline, or salts or esters thereof; for use in the prevention or treatment of neurotrauma, traumatic brain injury, cerebral palsy and spinal cord injury.

If the composition is a pharmaceutical product, such product may contain the daily dosage in one or more dosage units. The dosage unit may be in a liquid form or in a solid form, wherein in the latter case the daily dosage may be provided by one or more solid dosage units, e.g. in one or more capsules or tablets.

In another aspect of the present invention, the composition according to the invention may be used in a nutritional product comprising at least one component selected from the group of fats, proteins, and carbohydrates. It is understood that a nutritional product differs from a pharmaceutical product by the presence of nutrients which provide nutrition to the subject to which the composition is administered, in particular the presence of protein, fat, digestible carbohydrates and dietary fibres. It may further contain ingredients such as minerals, vitamins, organic acids, and flavouring agents. Although the term "nutraceutical product" is often used in literature, it denotes a nutritional product with a pharmaceutical component or pharmaceutical purpose. Hence, the nutritional composition according to the invention may also be used in a nutraceutical product.

The product of the invention is an enteral composition, intended for oral administration. It is preferably administered in liquid form. In one embodiment, the product comprises a lipid fraction and at least one of carbohydrates and proteins, wherein the lipid composition provides between 20 and 50 energy % of the food product. In one embodiment, the food product is a liquid composition containing between 0.8 and 1.4 kcal per ml.

Spinal Cord Injury, Neurotrauma and Cerebral Palsy

Age Associated Memory Impairment (AAMI) is a common condition characterized by very mild symptoms of cognitive decline that occur as part of the normal aging process. Symptoms of AAMI occur very gradually as a result of the normal aging process. In contrast, spinal cord injury (SCI), neurotrauma and cerebral palsy (CP) are conditions wherein the nervous tissue is abruptly damaged and the processes of neurodegeneration occur rapidly thereafter. Also, the functional impairments as a result of the injury appear instantly and impair affected individuals for the remaining of their lives. Further, a big contrast between the SCI/neurotrauma/CP and AAMI is that the problems in AAMI are per definition in the cognitive domain only, whereas SCI/neurotrauma/CP are characterized by the presence of a wide variety of problems such as non-cognitive motoric impairments. Because of the contrast between the non-cognitive problems after injury versus the cognitive problems in AAMI it is not obvious for the skilled person to consider the use of prior art compositions directed to e.g. Alzheimer's (AD), memory impairment, etc. for SCI or neurotrauma or CP, let alone to expect any effects on the non-cognitive aspects associated with SCI/neurotrauma/CP.

The method of the invention comprises administering the composition at outlined below to a person in need thereof, suffering from or at risk of conditions characterized by neuronal death and suboptimal neuronal survival. Such conditions include neurotrauma, traumatic brain injury, spinal cord injury, or other mechanistic events causing injury to the brain, like surgical measures, e.g. those occurring after brain tumor surgery. Persons at risk of developing such conditions are those involved in e.g. combating, e.g. military combat, in children at childbirth and due to an accident. As it appears, traumatic brain injury is the most prevalent injury of soldiers in combat (e.g. amongst the US troops in Iraq and Afghanistan).

According to one embodiment, the products comprising the composition according to the invention are intended for administration to humans, in particular children.

In one aspect, the invention is directed to a composition as described here below, for use in the prevention and/or treatment of conditions characterized by neuronal death and suboptimal neuronal survival. Such conditions include neurotrauma, traumatic brain injury, cerebral palsy, spinal cord injury, or other mechanistic events causing injury to the brain, like surgical measures, e.g. those occurring after brain tumor surgery.

Alternatively, the invention is directed at the use of a composition as described below in the manufacture of a composition for the prevention and/or treatment of conditions characterized by neuronal death and suboptimal neuronal survival. Such conditions include neurotrauma, traumatic brain injury, cerebral palsy, spinal cord injury, or other mechanistic events causing injury to the brain, like surgical measures, e.g. those occurring after brain tumor surgery.

The invention is particularly directed to the treatment of neurotrauma, brain injury, cerebral palsy and spinal cord injury, preferably at an SCI treatment.

DHA/EPA

The composition comprises at least one ω-3 polyunsaturated fatty acid (LC PUFA; having a chain length of 18 and more carbon atoms) selected from the group consisting of docosahexaenoic acid (22:6; DHA), eicosapentaenoic acid (20:5; EPA) and docosapentaenoic acid (22:5 co-3; DPA), preferably at least one of DHA and EPA. Preferably the present composition contains at least DHA, more preferably DHA and EPA. EPA is converted to DPA (ω-3), increasing subsequent conversion of DPA to DHA in the brain. Hence, the present composition preferably contains a significant amount of EPA, so to further stimulate in vivo DHA formation.

The DHA, EPA and/or DPA are preferably provided as triglycerides, diglycerides, monoglycerides, free fatty acids or their salts or esters, phospholipids, lysophospholipids, glycerol ethers, lipoproteins, ceramides, glycolipids or combinations thereof. Preferably, the present composition comprises at least DHA in triglyceride form.

In terms of daily dosage, the present method preferably comprises the administration of 500 to 5000 mg DHA+ EPA+DPA (preferably DHA+EPA) per day, more preferably 750 to 4000 mg per day, most preferably 1000 to 3000 mg per day. DHA is preferably administered in an amount of 500 to 5000 mg per day, more preferably 750 to 4000 mg per day, most preferably 1000 to 3000 mg per day. If at all, EPA is preferably administered in an amount of 500 to 5000 mg per day, more preferably 750 to 4000 mg per day, most preferably 1000 to 3000 mg per day. These amounts of EPA apply if it is used alone or in combination with DHA.

In terms of unit dosage, the proportion of DHA+EPA+ DPA (preferably DHA+EPA) of the total fatty acids is preferably 5 to 95 weight %, more preferably 10 to 80 weight %, most preferably 15 to 70 weight %. The present composition preferably comprises 5 to 95 weight % DHA based on total fatty acids, preferably 10 to 75 weight % DHA based on total fatty acids, more preferably 10 to 60 weight % DHA based on total fatty acids. The present composition preferably comprises 5 to 95 weight % EPA based on total fatty acids, preferably 10 to 75 weight % EPA, most preferably 15 to 60 weight %, based on total fatty acids.

The ratio of the weights of DHA to EPA is preferably larger than 1, more preferably 2:1 to 10:1, more preferably 3:1 to 8:1. The above-mentioned ratios and amounts take into account and optimise several aspects, including taste (too high LCP levels reduce taste, resulting in a reduced compliance), balance between DHA and precursors thereof to ensure optimal effectiveness while maintaining low-volume formulations.

Sources of DHA possible sources of DHA: tuna oil, (other) fish oils, DHA rich alkyl esters, algae oil, egg yolk, or phospholipids enriched with n-3 LCPUFA e.g. phosphatidylserine-DHA.

ALA/LA

It is preferred that the alpha-linolenic acid [ALA] content of the composition is maintained at low levels. The inventors believe that due to the inflammatory nature of neurotrauma, excess supply of highly unsaturated fatty acids increases the risk of further damage to injury tissue due to the effect of peroxidized PUFAs, even though it has been observed that in vivo supply of α-linolenic acid is neuroprotective in neurotrauma (King et al. J. Neurosci. (26) 17:4672-4680). While AD products mention 'normal' ALA levels of higher than 3 weight % of the fatty acids, i.e. about 5 weight %, it is discovered by the inventors that the ALA concentration is preferably maintained at levels less than 2.0 weight %, more preferably below 1.5 weight %, particularly below 1.0 weight %, calculated on the weight of all fatty acids. In the animal studies attached levels were about 0.8 g per 100 g fatty acids. These low ALA levels alone ('Control') however appeared ineffective.

Linoleic acid [LA] concentrations can be maintained at normal levels, i.e. between 20 to 30 weight %, although in one embodiment the LA concentration is also significantly reduced to an amount of <15 g/100 g fatty acids and even less than 10 weight %. The LA concentrations are preferably at least 1 weight % of the fatty acids.

In one embodiment, the weight ratio ω-3/ω-6 in the composition of the invention is preferably in the range 0.3 to 7, preferably in the range 1.4:1 to 5.9:1, more preferably in the range 3:1 to 5.5:1, most preferably 3:1 to 5:1, in particular less than 5:1. The amount of ω-6 LCPUFAs is preferably less than 50, preferably 5 to 40, more preferably 8 to 30 weight % of the fatty acids in the formula.

MCT

In one embodiment, the composition contains less than 5 weight %, preferably less than 2 weight % of fatty acids of less than 14 carbon atoms.

Medium chain fatty acids [MCT] are defined to be linear or branched saturated carboxylic acids having six (C6:0), seven (C7:0), eight (C8:0), nine (C9:0) or ten (C10:0) carbon atoms. The amount of MCTs are preferably lower than 2 weight %, more preferably lower than 1.5 weight %, most preferably lower than 1.0 weight % of the total fatty acids. In one embodiment, the sum of the medium chain fatty acids C6:0+C7:0+C8:0 over the sum of C9:0 and C10:0 is less than 2:1, more preferably less than 1.8:1, most preferably less than 1.6:1.

UMP

The present composition comprises uridine, cytidine and/ or an equivalent thereof, including salts, phosphates, acyl derivatives and/or esters. In terms of uridine, the composition preferably comprises at least one uridine or an equivalent thereof selected from the group consisting of uridine (i.e. ribosyl uracil), deoxyuridine (deoxyribosyl uracil), uridine phosphates (UMP, dUMP, UDP, UTP), nucleobase uracil and acylated uridine derivatives. In one embodiment, cytidine, CMP, citicoline (CDP-choline) may also be applied. Preferably, the present composition comprises an uridine phosphate selected from the group consisting of uridine monophosphate (UMP), uridine diphosphate (UDP) and uridine triphosphate (UTP); and/or a cytidine phosphate (CMP, CDP, CTP, preferably CMP). Most preferably the present composition comprises UMP, as UMP is most efficiently being taken up by the body. Preferably at least 50 weight % of the uridine in the present composition is provided by UMP, more preferably at least 75 weight %, most preferably at least 95 weight %. Doses that must be administered are given as UMP. The amount of uracil sources can be calculated taking the molar equivalent to the UMP amount.

The present method preferably comprises the administration of uridine (the cumulative amount of uridine, deoxyuridine, uridine phosphates, nucleobase uracil and acylated uridine derivatives) in an amount of (i) 0.1 to 6 g per day, preferably 0.2 to 3 g per day, more preferably 0.4 to 2 g per day, and/or (ii) 0.1 to 6 g per 100 ml (liquid) composition, preferably 0.2 to 3 g per 100 ml (liquid) composition, more preferably 0.4 to 2 g per 100 ml (liquid) composition. The above amounts also account for any amounts of cytidine, cytidine phosphates and citicoline incorporated in the composition or method.

Preferably, the present composition comprises uridine phosphate, preferably uridine monophosphate (UMP). The UMP is very efficiently taken up by the body. Hence, inclusion of UMP in the present composition enables a high effectivity at the lowest dosage and/or the administration of a low volume to the subject.

Choline

The present composition contains choline, a choline salt and/or choline ester. The choline salt is preferably selected from choline chloride, choline bitartrate, or choline stearate. The choline ester is preferably selected from a phosphatidylcholine and lyso-phosphatidyl choline. The present method preferably comprises the administration of more than 50 mg choline per day, preferably 80 to 3000 mg choline per day, more preferably 100 to 2000 mg choline per day, most preferably 150 to 1000 mg choline per day. The present composition preferably comprises 80 mg to 3000 gram choline per 100 ml of the liquid composition, preferably 100 mg to 2000 mg choline per 100 ml, preferably 200 to 1000 mg choline per 100 ml composition, most preferably 200 mg to 600 mg choline per 100 ml. The above numbers are based on choline, the amounts of choline equivalents or sources can be calculated taking the molar equivalent to choline into account.

Phospholipids

It is preferred to incorporate at least one phospholipid in the composition. The term "phospholipid" excludes PC that is already accounted for in the choline fraction. The present composition preferably comprises at least one phospholipid in an amount of 0.01 to 1 gram per 100 ml, more preferably between 0.05 and 0.5 gram per 100 ml, most preferably 80 to 600 mg per 100 ml. The at least one phospholipid is preferably provided for using lecithin.

Vitamins

The present combination comprises at least one B complex vitamin. The vitamin B is selected from the group of vitamin B1 (thiamine), vitamin B2 (riboflavin), vitamin B3 (niacin or niacinamide), vitamin B5 (pantothenic acid), vitamin B6 (pyridoxine, pyridoxal, or pyridoxamine, or pyridoxine hydrochloride), vitamin B7 (biotin), vitamin B9 (folic acid or folate), and vitamin B12 (various cobalamins). Functional equivalents are encompassed within these terms.

Preferably, at least one vitamin B is selected from the group of vitamin B6, vitamin B12 and vitamin B9. Preferably the present composition comprises at least two selected from the group consisting of vitamin B6, vitamin B12 and vitamin B9. In particular, good results have been achieved with a combination comprising vitamin B6, vitamin B12 and vitamin B9.

The vitamin B is to be administered in an effective dose, which dose depends on the type of vitamin B used. As a rule of thumb, a suitable minimum or a maximum dose may be chosen based on known dietary recommendations, for instance as recommended by Institute of Medicine (TOM) of the U.S. National Academy of Sciences or by Scientific Committee on Food (a scientific committee of the EU), the information disclosed herein and optionally a limited amount of routine testing. A minimum dose may be based on the estimated average requirement (EAR), although a lower dose may already be effective. A maximum dose usually does not exceed the tolerable upper intake levels (UL), as recommended by IOM.

If present in the nutritional composition or medicament, the vitamin B6 is usually present in an amount to provide a daily dosage in the range of 0.1 to 100 mg, in particular in the range of 0.5 to 25 mg, more in particular in the range of 0.5 to 5 mg. The present composition preferably comprises 0.1 to 100 mg vitamin B6 per 100 g (liquid) product, more preferably 0.5 to 5 mg vitamin B6 per 100 g (liquid) product, more preferably 0.5 to 5 mg vitamin B6 per 100 g (liquid) product.

If present in the nutritional composition or medicament, the vitamin B12 is usually present in an amount to provide a daily dosage in the range of 0.5 to 100 µg, in particular in the range of 1 to 10 µg, more in particular in the range of 1.5 to 5 µg. The present composition preferably comprises 0.5-100 µg vitamin B12 per 100 g (liquid) product, more preferably 1 to 10 µg vitamin B12 per 100 g (liquid) product, more preferably 1.5 to 5 µg vitamin B12 per 100 g (liquid) product. The term "vitamin B12" incorporates all cobalbumin equivalents known in the art.

If present in the nutritional composition or medicament, the vitamin B9 is usually present in an amount to provide a daily dosage in the range of 50 to 5000 µg, in particular in the range of 100 to 1000 µg, more in particular in the range of 200 to 800 µg. The present composition preferably comprises 50 to 5000 µg folic acid per 100 g (liquid) product, more preferably 100 to 1000 µg folic acid per 100 g (liquid) product, more preferably 200 to 800 µg folic acid per 100 g (liquid) product. Folates include folic acid, folinic acid, methylated, methenylated and formylated forms of folates, their salts or esters, as well as their derivatives with one or more glutamic acid, and all in either reduced or oxidized form.

Vitamins C, E

Vitamin C, or a functional equivalent thereof, may be present in an amount to provide a daily dosage in the range of 20 to 2000 mg, in particular in the range of 30 to 500 mg, more in particular in the range of 75 to 150 mg. In one embodiment, vitamin C, or a functional equivalent thereof, is present in an amount in the range of 20 to 2000 mg, in particular in the range of 30 to 500 mg, more in particular in the range of 75 to 150 mg per 100 ml of the composition.

Tocopherol and/or an equivalent thereof (i.e. a compound having vitamin E activity) may be present in an amount to provide a daily dosage in the range of 10 to 300 mg, in particular in the range of 30 to 200 mg, more in particular in the range of 35 to 100 mg, to prevent oxidative damage to the injury site resulting from dietary PUFA. In one embodiment, tocopherol and/or equivalent is present in an amount in the range of 10 to 300 mg, in particular in the range of 30 to 200 mg, more in particular in the range of 35 to 100 mg per 100 ml of the composition. The term "tocopherol and/or an equivalent thereof", as used in this description, comprises tocopherols, tocotrienols, pharmaceutical and/or nutritional acceptable derivatives thereof and any combination thereof. The above numbers are based on tocopherol equivalents, recognized in the art.

Selenium

The present composition preferably contains selenium. The antioxidant activity of selenium advantageously prevents and/or inhibits damages to the brain areas. Preferably the present method provides the administration of a composition comprising 0.01 and 5 mg selenium per 100 ml liquid product, preferably 0.02 and 0.1 mg selenium per 100 ml liquid product. The amount of selenium administered per day is preferably more than 0.01 mg, more preferably 0.01 to 0.5 mg.

Protein

Although the composition may further comprise proteinaceous material, it has been found that such component is not deemed necessary to achieve excellent SCI repair. In fact, it is thus possible to concentrate the actives in a low volume composition. Should a protein fraction be included, the protein fraction comprises intact proteins, peptides as may be obtained by hydrolyses of intact proteins and by syntheses, derivatives of peptides comprising more than 80 weight % amino acids. Nitrogen from nucleosides material and choline will not be calculated as being protein.

It is preferred that the amount of taurine (including taurine salts) is less than 0.1 g, preferably less than 0.05 g per daily dose. Additionally or alternatively, it is preferred that the amount of taurine (including taurine salts) is less than 5 mg, more preferably less than 2.5 g per 100 g composition.

In one embodiment, the composition comprises less than 25 mg, more preferably less than 20 mg, most preferably less than 15 mg cysteine and taurine per 100 ml of the (liquid) composition. In one embodiment, the composition comprises less than 25 mg, more preferably less than 20 mg, most preferably less than 15 mg cysteine per 100 ml of the (liquid) composition. It is preferred that the protein fraction comprises more than 70 weight % of casein or caseinates, or hydolysates thereof, and more preferably 80 weight % or more, because caseins comprise relatively low amounts of cysteine compared to other protein sources. It is further preferred to heat the liquid composition in order to oxidize the cysteine molecules present in the protein. This impairs biological availability of any residual cysteine as present in the formula. A preferred heat treatment involves sterilization. It is preferred to maintain the temperature remains below 135° C., preferably less than 132° C. combined with a sufficient long time to have the cysteine oxidized, i.e. more than 30 seconds, preferably more than 40 seconds.

In one embodiment, it is preferred that the composition has a protein content of less than 15 en %, more preferably less than 10 en %, most preferably less than 5 en % of the total energy content of the composition. The energy percentages of the components are calculated using the calculation factors 9 kcal per g lipid, 4 kcal per g protein or g digestible carbohydrates, 2 kcal per g dietary fibers and zero kcal for the other components in the composition. In one embodiment, it is preferred that the composition comprises less than 0.5 to 10 g protein per 100 ml, more preferably less than 1 to 6 gram protein per 100 ml, most preferably 2 to 6 gram protein/100 ml.

Molybdenum/Manganese

It has been found that enhanced levels of manganese and molybdenum are not necessary in the method according to the invention to achieve a beneficial effect on SCI and neurotrauma, and the like.

The amount of manganese consumed/administered in the method of the invention is preferably less than 300 µg per 100 ml, preferably less than 250 µg per 100 ml, more preferably less than 100 µg per 100 ml, in particular less than 60 µg per 100 ml. In one embodiment, the amount of manganese administered per day is preferably less than 100 µg, more preferably less than 50 µg.

In one embodiment, 100 ml liquid composition according to the invention comprises less than 0.05 mg molybdenum, preferably less than 0.025 mg molybdenum.

In one embodiment, the composition according to the invention comprises per 100 ml of liquid, preferably water:

100-500 mg, preferably about 300 mg EPA,
1000-1500 mg, preferably about 1200 mg DHA,
80-600 mg, preferably about 106 mg phospholipids,
200-600 mg, preferably about 400 mg choline,
400-800 mg, preferably about 625 mg UMP (uridine monophosphate),
20-60 mg, preferably about 40 mg vitamin E (alpha-TE),
60-100 mg, preferably about 80 mg vitamin C,
40-80 µg, preferably about 60 µg selenium,
1-5 µg, preferably about 3 µg vitamin B12,
0.5-2 mg, preferably about 1 mg vitamin B6, and
200-600 µg, preferably about 400 µg folic acid.

The compositions as described above can be used as a nutritional therapy, nutritional support, as a medical food, as a food for special medical purposes or as a nutritional supplement. Such product can be consumed at one, two or three servings of 125 mL per day during recovery and/or rehabilitation from neurotrauma.

The efficacy of the product can be established by testing recovery of the patient after neurotrauma e.g. assessing the rate of disability, post-traumatic amnesia duration, satisfaction of life, psychological status, cognitive ability to perform activities of daily living, level of functioning and employability, orientation to place, time, and personal information, executive control, working memory, verbal initiation and fluency, verbal learning, attention and psychomotorspeed, visual working memory, neuropsychological functioning. The product can be used to improve functional recovery, physical abilities, movement abilities of extremities, ability to coordinate muscle groups, sensory function, headache, dizziness, function, to decrease the loss of mobility, to reduce social and cognitive impairment, and to reduce (partial) loss of independence due to reduced physical abilities, employment, financial management.

EXAMPLES

1. Example 1: Preferred Ranges of the Products

TABLE 1

|  | Ranges for claimed products (mg/100 kJ) | Complete infant (mg/100 kJ) | Fortifier (mg/100 kJ) | Complete Adult (mg/100 kJ) |
| --- | --- | --- | --- | --- |
| DHA | 7-240 | 7-50 | 50-120 | 120-240 |
| DHA + EPA | 9-300 | 9-70 | 70-150 | 150-300 |
| UMP, CMP | 1.5-130 | 1.5-20 | 3-130 | 35-130 |
| UMP + CMP | 3-130 | 3-30 | 6-130 | 50-130 |
| Choline | 1-300 | 4-10 | 1-60 | 60-300 |

Example 2: Liquid Product Containing Per 125 ml Serving

Energy, kcal 125
Protein, g 3.8
Carbohydrate, g 16.5
Fat, g 4.9
EPA, mg 300
DHA, mg 1200
Phospholipids, mg 106
Choline, mg 400
UMP (uridine monophosphate), mg 625
Vitamin E (alpha-TE), mg 40
Vitamin C, mg 80
Selenium, µg 60
Vitamin B12, µg 3
Vitamin B6, mg 1
Folic acid, µg 400

Sodium, mg 125
Potassium, mg 187.5
Chloride, mg 156.3
Calcium, mg 100
Phosphorus, mg 87.5
Magnesium, mg 25.0
Iron, mg 2
Zinc, mg 1.5
Iodine, µg 16.3
Manganese, mg 0.41
Copper, µg 225
Molybdenum, µg 12.5
Chromium, µg 8.4
Vitamin A, µg 200
Thiamin (B1), mg 0.19
Riboflavin (B2), mg 0.20
Niacin (B3), mg NE 2.25
Pantothenic acid (B5), mg 0.66
Vitamin D, µg 0.88
Biotin, µg 5.0
Vitamin K, µg 6.6

Abbreviations: EPA, eicosapentaenoic acid; DHA, docosahexaenoic acid;

TE, tocopherol equivalents; NE, niacin equivalents.

Example 3: Product for Use in the Treatment of Cerebral Palsy

The product was tested in young infants who were diagnosed as suffering from cerebral palsy. The product comprised the active components according the invention. The product can be used to prepare a liquid formula which can be consumed by the infant separately from the normal milks, or be used as an additive to or fortifier of normal baby food or baby milk. In the experiment the latter way of administering was selected. A small amount of the fortifier (1.3 g) was added to a standard aliquot of dry baby milk powder (about 13-15 g according the product manual) to arrive at a final ready to feed standard baby milk.

The fortifier comprised the actives as indicated below in 1.3 g dry powder. Control and intervention product provided similar amounts of the other food components.

| Active ingredients | Active (mg/100 ml) | Control (mg/100 ml) |
|---|---|---|
| DHA + EPA | 30 | 0 |
| UMP + CMP | 2.4 | 0 |
| Choline | 7 | 0 |
| Vitamin B12 | 0.08 µg (0.12 µg/100 kcal) | 0.1 µg/100 kcal |
| Zn | 0.5 (0.76 mg/100 kcal) | 0.5 mg/100 kcal |
| Iodide | 10 µg (15.2 µg/100 kcal) | 10 µg/100 kcal |

A beneficial efficacy of the administration of the product on nervous tissue function and neuro-developmental outcome was measured by using imaging and state of the art diagnosing techniques.

Part 1: Exploration of the Neuroprotective Effects of DHA and UMP

Female adult Sprague-Dawley rats (~250 g) were used in this project. The spinal cord of all animals was injured at thoracic level T12 (T12) using a static compression model (Nystrom et al., 1988; Huang et al., 2007). Manual bladder expression was performed twice a day until the establishment of reflex voiding. Two sets of animals were studied: some were sacrificed at 5 weeks and others at 7 weeks post-injury, and the data were combined since they were not statistically different.

In the first part of the project, animals received the following treatments:
Group I: control diet (n=8)
Group II: UMP diet (n=9)
Group III: UMP+DHA diet (n=9)
Group IV: DHA diet (n=9)

A detailed description is given in Table 1.

Animals were sacrificed and perfused as described previously (Huang et al., 2007) at 5 or 7 weeks after injury, for immunohistochemical analysis of the spinal cord tissue.

All animals received fresh diet pellets daily, control or supplemented, starting immediately after SCI. Rats were treated with control dietary pellets or pellets enriched with the correspondent compounds. The operator was blind to the treatment given to the animals.

The individual's daily consumption of chow was monitored prior to the beginning of the study and the amount of DHA preparation and other compounds added to the chow calculated correspondingly.

Food was weighed every day to allow us to monitor the amount of food eaten in each cage (3 animals per cage).

Animals were monitored constantly for any adverse effects, and weighed regularly. They were analysed both behaviourally using the Basso, Beattie, Bresnahan locomotor rating scale (BBB) (Basso, Beattie and Bresnahan; Basso et al., 1995) and BBB subscore scale (Lankhorst et al., 1999) and histologically at the end of the experiment, using NeuN as a general neuronal marker to examine survival of spinal cord neurons. BBB assesses the hindlimb locomotor function, including the degree of joint movement, the limb coordination and the plantar placement of paw. The BBB subscore scale evaluates the higher motor function of the animals such as toe clearance, predominant paw position, instability and tail position (see appendix for details). The behavioural analysis was carried out every day for the first week, then at day 10 and finally once a week until the end of the experiment.

Transverse tissue sections from the injury epicentre were processed for neuronal nuclei (NeuN) immunohistochemistry. NeuN labels neuron-specific nuclear protein and has been repeatedly confirmed as a good marker of surviving neurons in injured adult rat spinal cord.

The statistical analysis of the data was carried out using one way or two way ANOVA, followed by pairwise post-hoc analysis using Bonferroni's test.

The results are plotted in FIG. 1.

Part 2: Exploration of the Neuroprotective Effects of Combinations of Food Components In the second part of our study, animals received the following treatments:
Group V: control diet (n=8)
Group VI: 'Invention diet' (n=8)

A detailed overview is given in Table 1, together with the diets of Part 1.

Figure 3:
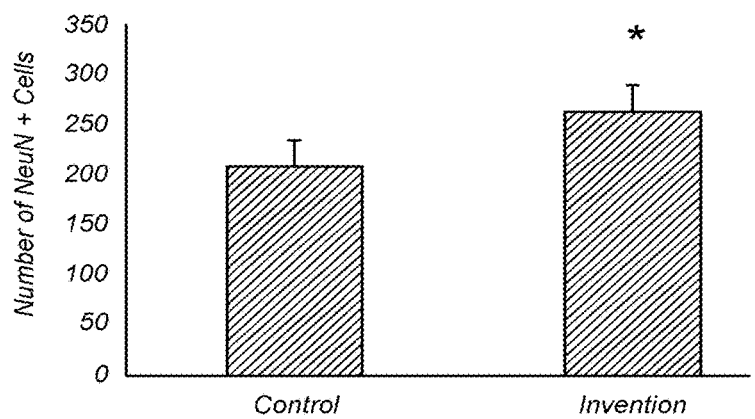
FIG. 3 shows the neuronal survival at 9 weeks post-injury for the control and the 'invention diet'.
Figure 4:
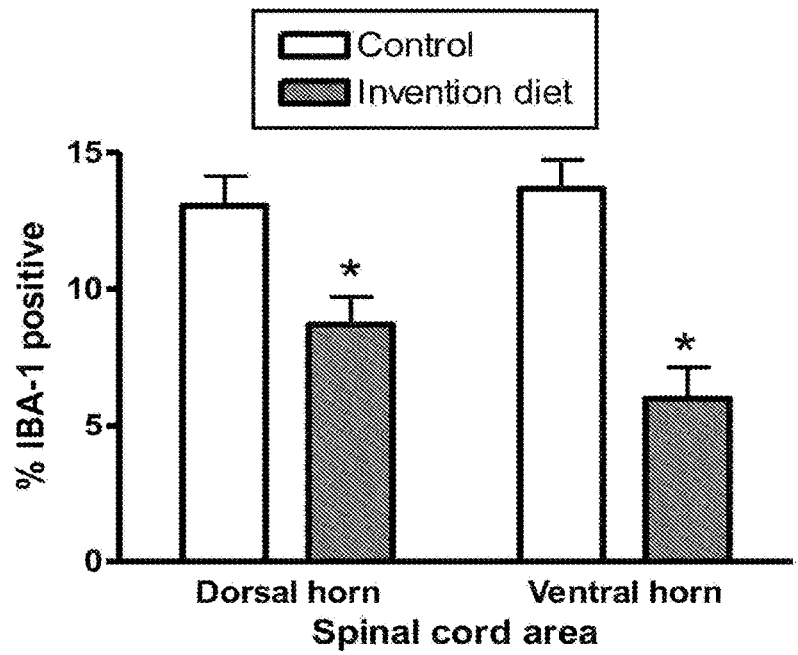
FIG. 4 shows the inflammatory response for the control and the 'invention diet' measured at the dorsal horn (left) and ventral horn (right) of the spinal cord area.

Animals received a compression SCI, as described previously, received the diets immediately after injury and were sacrificed at 9 weeks post-SCI. The whole experiment was conducted in the same way as it was in the first part except for the length of the project (9 weeks). A histological marker was added, to explore the inflammatory reaction (macrophages, FIG. 4) in spinal cord tissue. Sections were processed for immunohistochemistry using the following antibodies: NeuN (neuronal marker, FIG. 3), ED1 and IBA1

Figure 5:
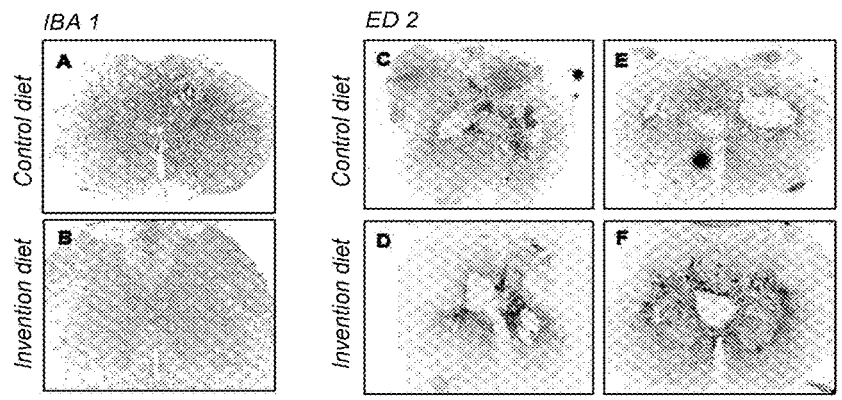
FIG. 5 shows the effect of SCI and the diet on IBA-I and ED1 immunoreactivity IBA1 and ED1 labeling of macrophages and microglia in animals fed on control and 'invention diet' and then sacrificed at 9 weeks post-injury. There appeared to be less IBA1 and ED1 immunoreactivity in 'invention diet' animals compared with control animals (B vs. A for IBA1 immunoreactivity; D and F vs. C and E for ED1 immunoreactivity). Quantitative analysis confirmed that IBA1 immunoreactivity in the DH=dorsal horn and VH=ventral horn was significantly reduced in 'invention diet' animals compared to controls ($*p<0.05$).
Figure 6:
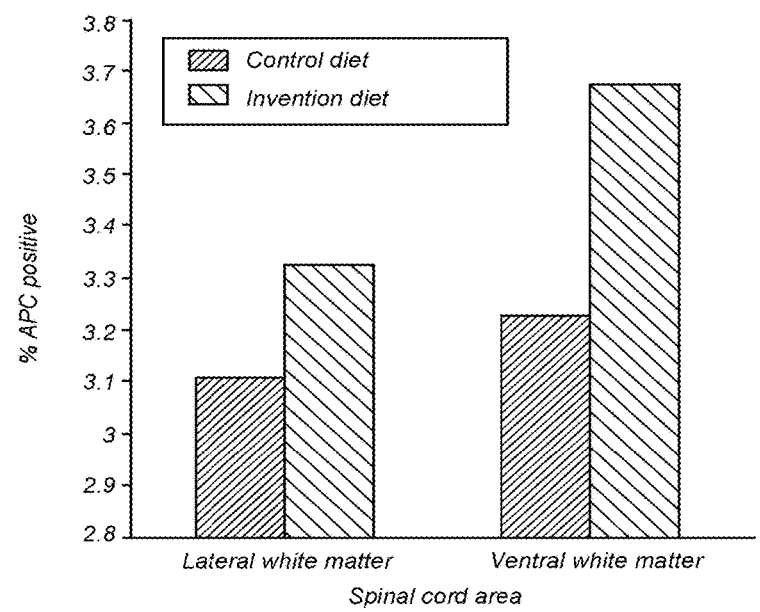
FIG. 6 shows the oligodendrocyte response for the control and the 'invention diet'.

(macrophage marker, FIG. 5) and APC (general oligodendroglial marker, FIG. 6).

Figure 2:
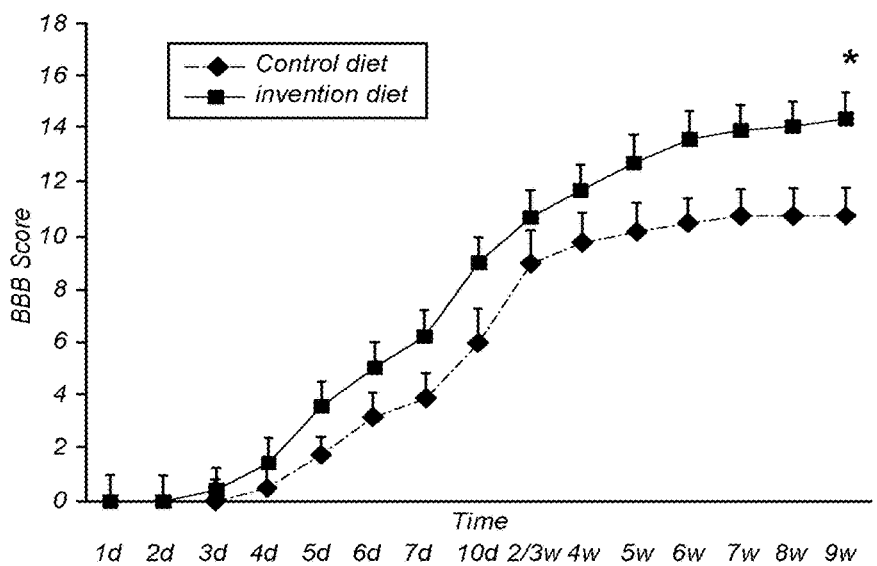
FIG. 2 shows the BBB score (locomotor recovery after SCI) over a period of 9 weeks for control (squares), and 'invention diet' (triangles).

The BBB scores are plotted in FIG. 2.

In summary this study shows that:
- animals fed on the 'invention diet' showed a clear improvement in locomotion when compared to the control;
- animals fed on the 'invention diet' showed a significantly increased neuronal survival at 9 weeks post-injury when compared to the control group and a significantly decreased macrophage recruitment The results show that the only protocol that gave statistically significant protection after injury was the supplementation with the 'invention diet' which leads to significant improvement in both neurological outcome and histological markers of injury after compression of the cord. The results with this oral dietary intervention are compelling, and on a par with some of the best neuroprotective substances studied so far in the field of SCI.

TABLE 1

Diet used in the experiments.

| Component | Control | DHA | UMP + Chol | DHA + UMP + Chol | Invention diet |
|---|---|---|---|---|---|
| UMP | — | — | 1.0 UMP | 1.0 UMP | 1.0 UMP |
| Fatty acids (% Fat fraction) | — 2.8% ALA | 13% DHA 2.5% ALA | — 2.7% ALA | 13% DHA 2.5% ALA | 13% DHA 0.79% ALA |
| Choline | 0.3% Choline | 0.3% Choline | 0.3% Choline | 0.3% Choline | 0.3% Choline |

Components are added to standard AIN-93 diet. All diets are iso-caloric indicating that intake of a fixed amount leads to the same caloric intake. All values are in grams per 100 grams of diet.

The invention claimed is:

1. A method for treating neurotrauma, traumatic brain injury, or cerebral palsy in a subject in need thereof, the method comprising administering to the subject a composition comprising:
   (i) one or more of uridine, cytidine, or salts or esters thereof;
   (ii) a lipid fraction comprising at least one of docosahexaenoic acid (22:6; DHA), eicosapentaenoic acid (20:5; EPA) and docosapentaenoic acid (22:5; DPA), and less than 2 weight % of α-linolenic acid (ALA), calculated on the weight of all fatty acids;
   (iii) choline, or salts or esters thereof; and
   (iv) at least one B complex vitamin selected from the group consisting of vitamin B6, vitamin B12 and vitamin B9.

2. The method according to claim 1 for treating traumatic brain injury or neurotrauma, said composition comprising (i) one or more of uridine, cytidine, or phosphates thereof.

3. The method according to claim 1, wherein the lipid fraction comprises medium chain fatty acids, wherein the sum of medium chain fatty acids C6:0+C7:0+C8:0 over the sum of C9:0 and C10:0 is less than 2:1.

4. The method according to claim 1, wherein the lipid fraction comprises fatty acids of less than 14 carbon atoms in an amount of less than 2 weight %, based on total fatty acids.

5. The method according to claim 1, wherein the composition further comprises cysteine and taurine in an amount of less than 25 mg of their sum per 100 ml of the composition.

6. The method according to claim 1, wherein the composition further comprises linoleic acid (LA) in an amount of less than 15 g/100 g fatty acids.

7. The method according to claim 6, wherein the B complex vitamin is selected from the group consisting of vitamin B6, B9 and B12.

8. The method according to claim 1, wherein the lipid fraction comprises 9 to 300 mg/100 kJ DHA+EPA+DPA.

9. The method according to claim 1, wherein the lipid fraction comprises 9 to 300 mg/100 kJ DHA+EPA.

10. The method according to claim 1, wherein the composition comprises 1.5 to 130 mg/100 kJ of one or more of uridine, cytidine, or salts, phosphates or esters thereof, calculated as uridine and cytidine.

11. The method according to claim 1, wherein the composition comprises 1 to 300 mg/100 kJ of choline, or salts or esters thereof, calculated as choline.

12. The method according to claim 1, wherein the composition further comprises one or more selected from the group consisting of vitamin C or vitamin E and selenium.

13. The method according to claim 1, wherein the composition further comprises at least one phospholipid.

14. The method according to claim 1, wherein the composition is a nutritional product.

15. The method according to claim 12, wherein the composition comprises, per 100 ml of liquid:
   100-500 mg EPA,
   1000-1500 mg DHA,
   80-600 mg phospholipids,
   200-600 mg choline,
   400-800 mg uridine monophosphate (UMP),
   20-60 mg alpha-TE (vitamin E),
   60-100 mg vitamin C,
   40-80 μg selenium,
   1-5 μg vitamin B12,
   0.5-2 mg vitamin B6, and
   200-600 μg folic acid.

16. The method according to claim 1, said composition comprising vitamin B6, B9 and B12.

17. A method for treating neurotrauma, traumatic brain injury, or cerebral palsy in a subject in need thereof, the method comprising administering to the subject a kit of parts comprising:
   i) one or more of uridine, cytidine, or salts or esters thereof;
   ii) a lipid fraction comprising at least one of docosahexaenoic acid (22:6; DHA), eicosapentaenoic acid (20:5; EPA) and docosapentaenoic acid (22:5; DPA), and less than 2 weight % of α-linolenic acid (ALA), calculated on the weight of all fatty acids;
   iii) choline, or salts or esters thereof; and
   iv) at least one B complex vitamin selected from the group consisting of vitamin B6, vitamin B12 and vitamin B9.

18. The method according to claim 17, said kit comprising (i) one or more of uridine, cytidine, or phosphates thereof.

19. The method according to claim 17, said kit comprising vitamin B6, B9 and B12.

20. The method according to claim 17, for treating traumatic brain injury or neurotrauma, said kit comprising (i) one or more of uridine, cytidine, or phosphates thereof.

21. The method according to claim 20, for treating traumatic brain injury.

22. The method according to claim 2, for treating traumatic brain injury.

23. The method according to claim 2, wherein the composition is a liquid composition with between 0.8 and 1.4 kcal per ml.

* * * * *